(12) United States Patent
Crooks et al.

(10) Patent No.: US 6,503,922 B2
(45) Date of Patent: Jan. 7, 2003

(54) BRIDGED NICOTINE COMPOUNDS FOR USE IN THE TREATMENT OF CNS PATHOLOGIES

(75) Inventors: Peter A. Crooks, Lexington, KY (US); Linda P. Dwoskin, Lexington, KY (US); Rui Xu, New York, NY (US); Vladimir P. Grinevich, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/941,926

(22) Filed: Aug. 30, 2001

(65) Prior Publication Data

US 2002/0099069 A1 Jul. 25, 2002

Related U.S. Application Data

(60) Provisional application No. 60/228,766, filed on Aug. 30, 2000.

(51) Int. Cl.[7] .................. A61K 31/4745; C07D 471/02
(52) U.S. Cl. .......................... 514/292; 546/84; 546/85; 546/88
(58) Field of Search ............................ 514/292; 546/84, 546/85, 88

(56) References Cited

U.S. PATENT DOCUMENTS 5,567,710 A    10/1996   Whitten et al.
5,691,365 A    11/1997   Crooks et al.

OTHER PUBLICATIONS

Charles G. Chavdarian, et al., "Bridged Nicotines, Synthesis of cis–2,3,3a,4,5,9b–Hexahydro–1–methyl–1H–pyrrolo[2,3–f]quinoline", American Chemical Society, J. of Org. Chem., 1983, 48, pp. 492–494.

William Glassco, et al., "Synthesis, Optical Resolution, Absolute Configuration, and Preliminary Pharmacology of (+)–and (-)-cis 2,3,3a,4,5,9b–Hexahydro–1–methyl–1H–pyrrolo-[3,2–h] isoquinoline, a Structural Analog of Nicotine", American Chemical Society, J. of Org. Chem., 1993, 36, pp. 3381–3385.

*Primary Examiner*—C. S. Aulakh
(74) *Attorney, Agent, or Firm*—McDermott, Will & Emery

(57) ABSTRACT

Pharmaceutical compounds comprising bridged nicotine analogs of N-octylnicotinium iodide (NONI) having selective antagonist properties at α3β2-containing nicotinic receptor subtypes, and compositions containing these compounds. The compounds and compositions are used to treat central nervous system pathologies.

36 Claims, No Drawings

BRIDGED NICOTINE COMPOUNDS FOR USE IN THE TREATMENT OF CNS PATHOLOGIES

RELATED APPLICATION

This application claims priority from U.S. Provisional Patent Application Serial No. 60/228,76, filed Aug. 30, 2000, incorporated herein by reference.

FIELD OF THE INVENTION

This invention relates to bridged nicotine analogs of N-octylnicotinium iodide (NONI) that have selective antagonist properties at α3β2-containing nicotinic receptor subtypes and to a method of using such compounds to treat central nervous system pathologies. The present invention also relates to pharmaceutical compositions containing these compounds, as well as various uses thereof.

BACKGROUND OF THE INVENTION

Formula (I) below shows the structure of S-(−)-nicotine (NIC), which activates neuronal nicotinic receptors evoking release of dopamine (DA) from presynaptic terminals in the central nervous system (CNS). NIC is a legal substance of dependence that produces many of its effects on the CNS, some of which may be considered to be beneficial, e.g., mood elevation, arousal and learning and memory enhancement. NIC produces its effect by binding to a family of ligand-gated ion channels, stimulation by acetylcholine (ACh) or NIC causes the ion channel to open, and cations to flux with a resulting rapid (in msec) depolarization of the target cell.

Over the last 12 years, there has been a substantial increase in studies on brain nicotinic receptors. These nicotinic receptors are composed of four subunit domains: 2α, β, γ and δ or ε. Neuronal nicotinic receptors are composed of only two subunits, α and β and are believed to assemble with the general stoichiometry of 2α and 3β. Eight subtypes of the α subunit (α2 to α9) and three subtypes of the β unit (β2 to β4) are found in CNS. The most common nicotinic receptor species in the brain is composed of two α4 and three β2 subunits, i.e., α4β2. These subunits display different, but overlapping, patterns of expression in the brain.

For the most part, the actual subunit compositions and stoichiometries of nicotinic receptors in the brain remain to be elucidated. Thus, neuronal nicotinic receptor subtype diversity originates from differences in the amino acid sequence at the subunit level and from the multiple combinations of assemblies of subunits into functional receptor proteins afford wide diversity of pharmacological specificity.

In spite of the extensive diversity in neuronal nicotinic receptor messenger RNA expression, only a limited number of tools are available to study the pharmacology of native receptors. Radioligands are used in many such studies. [$^3$H]NIC appears to label the same sites in the brain as [$^3$H]ACh. It has been estimated that over 90% of [$^3$H]NIC binding in the brain is due to association with a receptor that is composed of α4 and β2 subunits. Also, nicotinic receptor subtypes can be studied using an assay such as NIC-evoked [$^3$H]DA release from rat straital slices. Nicotinic receptors are located in the cell body and terminal areas of the nigrostriatal system. NIC facilitates DA release from striatal nerve terminals. Studies strongly suggest that the [$^3$H]DA release assay is useful to probe the α3β2-containing subtype of the nicotinic receptor.

The structural and functional diversity of CNS nicotinic receptors has stimulated a great deal of interest in developing novel, subtype-selective agonists. Some of these agonists are currently being evaluated in clinical trials for cognitive enhancement and neuroprotective effects potentially beneficial for diseases such as Alzheimer's and Parkinson's Disease. Surprisingly, little attention a has been focused on developing subtype-selective antagonists for neuronal nicotinic receptors.

A class pyridino N-substituted nicotine analogs having formula (II) below are known antagonists that inhibit nicotine evoked [$^3$H]DA release from dopaminergic nerve terminals in the brain. The abbreviated nomenclature is given in parentheses.

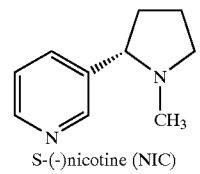

S-(−)nicotine (NIC)

I

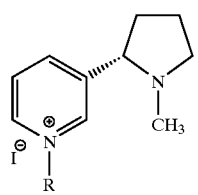

II a) R = − (CH$_2$)$_7$CH$_3$ (NONI)
b) R = − (CH$_2$)$_8$CH$_3$ (NNNI)
c) R = − (CH$_2$)$_9$CH$_3$ (NDNI)
d) R = − (CH$_2$)$_{10}$CH$_3$ (NUNI)
e) R = − (CH$_2$)$_{11}$CH$_3$ (NDDNI)

These compounds are useful in the treatment of nicotine abuse, smoking cessation therapy, as an antidote for nicotine intoxication, treatment of cognitive disorders such as Alzheimer's disease and for the treatment of Parkinson's disease. The compounds and their method of use were the subject of U.S. Pat. No. 5,691,365, issued Nov. 25, 1997. The content of this patent is incorporated herein by reference.

The invention disclosed herein is directed to another new class of efficacious and subtype-selective nicotinic antagonists at nicotinic receptors in the CNS. These compounds comprise bridged nicotine analogs of NONI.

SUMMARY OF THE INVENTION

The present invention provides; for bridged nicotine analogs of N-octylnicotinium iodide (NONI) compounds having potent and selective antagonistic activity at neuronal nicotinic receptor subtypes. The compounds competitively inhibit CNS acting nicotinic receptor agonists that are acting as putative α3β2 neuronal nicotinic receptor in the CNS.

A preferred embodiment of the invention provides for a method of antagonizing the nicotinic receptor comprising administering of a pharmaceutically effective amount of a compound of the invention.

Still another embodiment the invention provides a method for the treatment of psychostimulant abuse (including nicotine abuse, amphetamine abuse, methamphetamine abuse, alcohol abuse and cocaine abuse), as smoking cessation therapy, as an antidote for nicotine intoxication comprising administering of a pharmaceutically effective amount of a compound according to the invention, as a therapeutic agent for the treatment of pathologies of the GI tract, including irritable bowel syndrome, colitis and related disorders.

This invention further provides a method of treatment of CNS disorders associated with the alteration of normal neurotransmitter release in the brain, including conditions such as Alzheimer's disease as well as other types of dementia, Parkinson's disease, cognitive dysfunction (including disorders of attention, focus and concentration), attention deficit syndrome, affective disorders, mood and emotional disorders such as depression, panic anxiety and psychosis, Tourette's syndrome, schizophrenia, eating disorders and the control of pain comprising administering of a pharmaceutically effective amount of a compound according to the invention.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

DETAILED DESCRIPTION OF THE INVENTION

The present invention provides, novel bridged-ring compounds corresponding to the schematic structure formulas III and IV below:

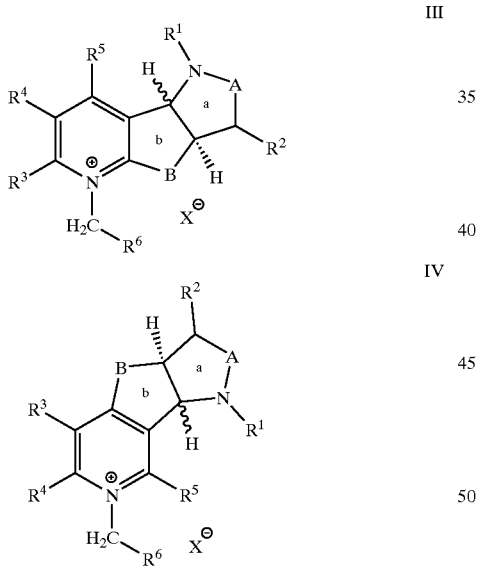

wherein

A is a 1, 2 or 3 atom bridging species selected from straight chain or branched chain alkylene moiety having up to 3 atoms in the backbone thereof, or a substituted alkenylene moiety having up to 3 atoms in the backbone thereof, or a C(O), O, C(S), S, S(O) or S(O)$_2$ containing alkylene moiety, provided however, that any heteroatom contained in A is separated from N by at least one carbon atom;

B is a 1, 2 or 3 atom bridging species selected from straight chain or branched chain alkylene moiety having up to 3 atoms in the backbone thereof, or a substituted alkenylene moiety having up to 3 atoms in the backbone thereof, or a C(O), O, N(Y$^1$), C(S), S, S(O) or S(O)$_2$ containing alkene moiety, wherein Y$^1$ is hydrogen or lower alkyl or aryl;

R$^1$ is selected from hydrogen, lower alkyl (e.g., C$_1$–C$_{10}$ alkyl, preferably C$_1$–C$_6$ alkyl, and more preferably methyl, ethyl, isopropyl or isobutyl) or an aromatic group-containing species;

R$^2$ is selected from hydrogen or lower alkyl;

R$^3$, R$^4$ and R$^5$ are each independently selected from hydrogen; alkyl; substituted alkyl; cycloalkyl; substituted cycloalkyl; alkenyl; substituted alkenyl; alkynyl; substituted alkynyl; aryl; substituted aryl; alkylaryl; substituted alkylaryl; arylalkyl; substituted arylalkyl; arylalkenyl; substituted arylalkenyl; arylalkynyl; substituted arylalkynyl; heterocyclic; substituted heterocyclic; trifluoromethyl; halogen; cyano; nitro; S(O)Y$^2$, S(O)$_2$Y$^2$, S(O)$_2$OY$^2$ or S(O)$_2$NHY$^2$, wherein each Y$^2$ is independently hydrogen, lower alkyl, alkenyl, alkynyl or aryl, provided, however, that when R$^3$, R$^4$ or R$^5$ is S(O)Y$^2$, Y$^2$ is not hydrogen, and further provided that when Y$^2$ is alkenyl or alkynyl, the site of unsaturation is not conjugated with a heteroatom; C(O)Y$^3$, wherein Y$^3$ is selected from hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, arylalkenyl, substituted arylalkenyl, arylalkynyl, substituted arylalkynyl, heterocyclic, substituted heterocyclic or trifluoromethyl, provided, however, that the carbonyl functionality is not conjugated with an alkenyl or alkynyl functionality; OY$^4$ or N(Y$^4$)$_2$ wherein each Y$^4$ is independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, acyl, trifluoromethyl, alkylsulfonyl or arylsulfonyl, provided, however, that the OY$^4$ or N(Y$^4$)$_2$ functionality is not conjugated with an alkenyl or alkynyl functionality; SY$^5$ wherein Y$^5$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic or trifluoromethyl, provided, however, that the SY$^5$ functionality is not conjugated with an alkenyl or alkynyl functionality;

R$^6$ is selected from alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, heterocyclic or substituted heterocyclic; and X is selected from chlorine, bromine, iodine, HSO$_4$, 1/2SO$_2$, CH$_3$SO$_3$, p-TsO or CF$_3$SO$_3$.

The junction between rings a and b can be either cis or trans geometry. The present invention includes all possible diastereomers and all enantiomeric forms as well as racemic mixtures. The compounds can be separated into substantially optically pure compounds. The compounds of the invention are nicotinic receptor antagonists. They inhibit NIC-evoked [$^3$H]-DA release and inhibit [$^3$H]-NIC binding.

It is preferred that A is either $CH_2$ or $CH_2CH_2$; B is $CH_2$, $CH_2CH_2$ or $N(Y^1)$ where $Y^1$ is either hydrogen or methyl; $R^1$ is a $C_1$–$C_{10}$ alkyl or more preferably a $C_1$–$C_6$ alkyl or even more preferably a $C_1$–$C_4$ alkyl such as a methyl, ethyl, isopropyl or isobutyl; $R^2$ is hydrogen; $R^3$, $R^4$ and $R^5$ are individually selected from the group consisting of hydrogen, halogen, alkyl and alkanoyl; $R^6$ is a $C_4$–$C_{19}$ unbranched alkyl; and X is iodine.

As employed herein, the meaning of the aforementioned terms are defined as follows:

"lower alkyl" refers to straight or branched chain alkyl radicals having in the range of 1 up to 4 carbon atoms;

"alkyl" refers to straight or branched chain alkyl radicals having in the range of 1 up to 19 carbon atoms and "substituted alkyl" refers to alkyl radicals further bearing one or more substituents such as hydroxy, alkoxy (of a lower alkyl group), mercapto (of a lower alkyl group), aryl, heterocyclic, halogen, trifluoromethyl, cyano, nitro, amino, carboxyl, carbanate, sulfonyl, sulfonamide, and the like.

"cycloalkyl" refers to cyclic ring-containing radicals containing in the range of 3 up to 8 carbon atoms and "substituted cycloalkyl" refers to cycloalkyl radicals further bearing one or more substituent as set forth above;

"alkenyl" refers to straight or branched chain hydrocarbyl radicals having at least one carbon-carbon double bond, and having in the range of 2 up to 19 carbon atoms and "substituted alkenyl" refers to alkenyl radicals further bearing one or more substituents as set forth above;

"alkynyl" refers to straight or branched chain hydrocarbyl radicals having at least one carbon-carbon triple bond, and having in the range of 2 up to 19 carbon atoms and "substituted alkynyl" refers to alkynyl radicals further bearing one or more substituents as set forth above;

"aryl" refers to aromatic radicals having in the range of 6 up to 24 carbon atoms and "substituted aryl" refers to aryl radicals further bearing one or more substituents as set forth above;

"alkylaryl" refers to alkyl-substituted aryl radicals and "substituted alkylaryl" refers to alkylaryl radicals further bearing one or more substituents as set forth above;

"arylalkyl" refers to aryl-substituted alkyl radicals and "substituted arylalkyl" refers to arylalkyl radicals further bearing one or more substituents as set forth above;

"arylalkenyl" refers to aryl-substituted alkenyl radicals and "substituted arylalkenyl" refers to arylalkenyl radicals further bearing one or more substituents as set forth above;

"arylalkynyl" refers to aryl-substituted alkynyl radicals and "substituted arylalkynyl" refers to arylalkynyl radicals further bearing one or more substituents as set forth above;

"aroyl" refers to aryl-substituted species such as benzoyl and "substituted aroyl" refers to aroyl radicals further bearing one or more substituents as set forth above;

"heterocyclic" refers to cyclic radicals containing one or more heteroatoms as part of the ring structure, and having in the range of, 3 up to 24 carbon atoms and "substituted heterocyclic" refers to heterocyclic radicals further bearing one or more substituents as set forth above; "acyl" refers to alkyl-carbonyl species;

"halogen" refers to fluoride, chloride, bromide or iodide radicals; and

"an effective amount", when used in reference to compounds of the invention, refers to doses of compound sufficient to provide circulating concentrations high enough to impart a beneficial effect on the recipient thereof. Such levels typically fall in the range of about 0.001 up to about 100 mg/kg/day, with levels in the range of about 0.05 up to about 10 mg/kg/day being preferred.

The novel compounds of this invention are substantially optically pure.

The bridged nicotine analogs of NONI include compounds having formulas V and VI. The abbreviated nomenclature is given in parentheses.

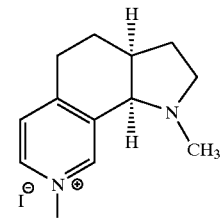

V a) R = - $(CH_2)_7CH_3$ (ACO)
b) R = - $(CH_2)_8CH_3$ (ACN)
c) R = - $(CH_2)_9CH_3$ (ACD)
d) R = - $(CH_2)_{10}CH_3$ (ACU)
e) R = - $(CH_2)_{11}CH_3$ (ACDD)

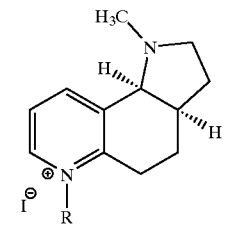

VI a) R = - $(CH_2)_7CH_3$ (BCO)
b) R = - $(CH_2)_8CH_3$ (BCN)
c) R = - $(CH_2)_9CH_3$ (BCD)
d) R = - $(CH_2)_{10}CH_3$ (BCU)
e) R = - $(CH_2)_{11}CH_3$ (BCDD)

These compounds potently, competitively and selectively inhibit dopamine release induced by nicotine in superfused rat striatal slice preparations, while exhibiting weak insignificant inhibition of [$^3$H]-nicotine and [$^3$H]-MLA binding to rat striatal membranes. These compounds include, but are not limited to, the following specific compounds:

cis-1-methyl-8-octyl-2,3,3a,4,5,9b-hexahydro-1H-pyrrolo [3,2-h]isoquinolin-8-ium iodide (ACO),
cis-1-methyl-8-nonyl-2,3,3a,4,5,9b-hexahydro-1H-pyrrolo [3,2-h]isoquinolin-8-ium iodide (ACN),
cis-8-decyl-1-methyl-2,3,3a,4,5,9b-hexahydro-1H-pyrrolo [3,2-h]isoquinolin-8-ium iodide (ACD),
cis-1-methyl-8-undecyl-2,3,3a,4,5,9b-hexahydro-1H-pyrrolo[3,2-h]isoquinolin-8-ium iodide (ACU),
cis-8-dodecyl-1-methyl-2,3,3a,4,5,9b-hexahydro-1H-pyrrolo[3,2-h]isoquinolin-8-ium iodide (ACDD).
cis-1-methyl-6-octyl-2,3,3a,4,5,9b-hexahydro-1H-pyrrolo [2,3-f]isoquinolin-6-ium iodide (BCO),
cis-1-methyl-6-nonyl-2,3,3a,4,5,9b-hexahydro-1H-pyrrolo [2,3-f]isoquinolin-6-ium iodide (BCN),
cis-6-decyl-1-methyl-2,3,3a,4,5,9b-hexahydro-1H-pyrrolo [2,3-f]isoquinolin-6-ium iodide (BCD),
cis-1-methyl-6-undecyl-2,3,3a,4,5,9b-hexahydro-1H-pyrrolo[2,3-f]isoquinolin-6-ium iodide (BCU), and
cis-6-dodecyl-1-methyl-2,3,3a,4,5,9b-hexahydro-1H-pyrrolo[2,3-f]isoquinolin-6-ium iodide (BCDD).

These compounds can be prepared from corresponding free bases by reaction with an appropriate alkyl iodide using techniques known to those skilled in the art of organic synthesis. The requisite free bases can be synthesized using the techniques set forth by Chavdarian et al., *J Org. Chem.* 48:492 (1983), Glassco et al., *J. Med. Chem.* 36:3381 (1993) and Vernier et al., *Bioorg. Med. Chem. Lett.* 8:2173 (1998).

The invention will now be described in greater detail by reference to the following non-limiting examples.

EXAMPLE 1

Preparation of cis-1-Methyl-8-octyl-2,3,3a,4,5,9b-hexahydro-1H-pyrrolo[3,2-h]-isoquinolin-8-ium iodide (ACO)

To a stirred solution of cis-1-methyl-2,3,3a,4,5,9b-hexahydro-1H-pyrrolo[3,2-h]isoquinoline (100 mg, 0.53 mmol) in AcOH (2 ml) was added 1-iodooctane (383 mg, 1.59 mmol). The mixture was heated at reflux under nitrogen for 3 days. AcOH was evaporated and the residue was dissolved in $CHCl_3$. The mixture was washed with saturated aqueous $NaHCO_3$, water and brine successively and dried. Evaporation of the solvent followed by titration with ether afforded 155 mg (68%) of cis-1-methyl-8-octyl-2,3,3a,4,5,9b-hexahydro-1H-pyrrolo[3,2-h]isoquinolin-8-ium iodide (ACO) as a brown oil. $^1$H NMR (300 MHz, $CDCl_3$) δ9.16 (1H, s, C9-H), 9.03 (1H, d, J6.0 Hz, C7-H), 7.82 (1H, d, J6.0 Hz, C6-H), 4.86 (2H, m. $pyCH_2$), 3.66 (1H, d, J8.4 Hz, C9b-H), 2.43 (3H, s, $NCH_3$), 1.55–3.20 (9H, m, $CH_2$+CH), 1.99 (2H, m, $pyCH_2CH_2$), 1.00–1.50 (10H, m, 5×$CH_2$), 0.81 (3H, t, J6.9 Hz, $CH_2CH_3$); $^{13}$C NMR (75 MHz, $CDCl_3$) δ161.8, 143.5, 142.5, 138.2, 127.6, 63.4, 61.4, 55.8, 41.2, 35.8, 32.1, 31.8, 30.0, 29.2×2, 27.8, 27.6, 26.2, 22.7, 14.2.

EXAMPLE 2

Preparation of cis-1-Methyl-8-nonyl-2,3,3a,4,5,9b-hexahydro-1H-pyrrolo[3,2-h]-isoquinolin-8-ium iodide (ACN)

To a stirred solution of cis-1-methyl-2,3,3a,4,5,9b-hexahydro-1H-pyrrolo[3,2-h]isoquinoline (120 mg, 0.64 mmol) in AcOH (2 ml) was added 1-iodononane (488 mg, 1.92 mmol). The mixture was heated at reflux under nitrogen for 3 days. AcOH was evaporated and the residue was dissolved in $CHCl_3$. The mixture was washed with saturated aqueous $NaHCO_3$, water and brine successively and dried. Evaporation of the solvent followed by titration with ether afforded 222 mg (79%) of cis-1-methyl-8-nonyl-2,3,3a,4,5,9b-hexahydro-1H-pyrrolo[3,2-h]isoquinolin-8-ium iodide (ACN) as a brown oil. $^1$H NMR (300 MHz, $CDCl_3$) δ9.05 (1H, s, C9-H), 9.03 (1H, d, J6.0 Hz, C7-H), 7.81 (1H, d, J6.0 Hz, C6-H), 4.88 (2H, m. $pyCH_2$), 3.47 (1H, d, J8.7 Hz, C9b-H), 2.36 (3H, s, $NCH_3$), 1.60–3.10 (9H, m, $CH_2$+CH), 2.00 (2H, m, $pyCH_2CH_2$), 1.10–1.50 (12H, m, 6×$CH_2$), 0.83 (3H, t, J6.9 Hz, $CH_2CH_3$); $^{13}$C NMR (75 MHz, $CDCl_3$) δ161.7, 143.4, 142.5, 139.2, 127.5, 63.5, 61.5, 55.9, 41.3, 35.9, 32.1, 32.0, 30.3, 29.5, 29.3, 29.2, 28.2, 27.6, 26.2, 22.8, 14.2.

EXAMPLE 3

Preparation of cis-8-Decyl-1-methyl-2,3,3a,4,5,9b-hexahydro-1H-pyrrolo[3,2-h]-isoquinolin-8-ium iodide (ACD)

To a stirred solution of cis-1-methyl-2,3,3a,4,5,9b-hexahydro-1H-pyrrolo[3,2-h]isoquinoline (80 mg, 0.43 mmol) in AcOH (2 ml) was added 1-iododecane (342 mg, 1.28 mmol). The mixture was heated at reflux under nitrogen for 3 days. AcOH was evaporated and the residue was dissolved in $CHCl_3$. The mixture was washed with saturated aqueous $NaHCO_3$, water and brine successively and dried. Evaporation of the solvent followed by titration with ether afforded 130 mg (67%) of cis-8-decyl-1-methyl-2,3,3a,4,5,9b-hexahydro-1H-pyrrolo[3,2-h]isoquinolin-8-ium iodide (ACD) as a brown oil. $^1$H NMR (300 MHz, $CDCl_3$) δ9.16 (1H, s, C9-H), 9.14 (1H, d, J5.4 Hz, C7-H), 7.82 (1H, d, J6.0 Hz, C6-H), 4.85 (2H, m. $pyCH_2$), 3.43 (1H, d, J8.4 Hz, C9b-H), 2.30 (3H, s, $NCH_3$), 1.50–3.10 (9H, m, $CH_2$+CH), 1.96 (2H, m, $pyCH_2CH_2$), 1.00–1.40 (14H, m, 7×$CH_2$), 0.78 (3H, t, J6.9 Hz, $CH_2CH_3$); $^{13}$C NMR (75 MHz, $CDCl_3$) δ161.5, 143.4, 142.7, 138.9, 127.5, 63.3, 61.2, 55.8, 41.0, 35.7, 32.1, 31.9, 30.1, 29.5, 29.4, 29.3, 29.2, 28.2, 27.3, 26.1, 22.7, 14.2.

EXAMPLE 4

Preparation of cis-1-Methyl-8-undecyl-2,3,3a,4,5,9b-hexahydro-1H-pyrrolo[3,2-h]-isoquinolin-8-ium iodide (ACU)

To a stirred solution of cis-1-methyl-2,3,3a,4,5,9b-hexahydro-1H-pyrrolo[3,2-h]isoquinoline (120 mg, 0.64 mmol) in AcOH (2 ml) was added 1-iodoundecane (542 mg, 1.92 mmol). The mixture was heated at reflux under nitrogen for 3 days. AcOH was evaporated and the residue was dissolved in $CHCl_3$. The mixture was washed with saturated aqueous $NaHCO_3$, water and brine successively and dried. Evaporation of the solvent followed by titration with ether afforded 210 mg (70%) of cis-1-methyl-8-undecyl-2,3,3a,4,5,9b-hexahydro-1H-pyrrolo[3,2-h]isoquinolin-8-ium iodide (ACU) as a brown oil. $^1$H NMR (300 MHz, $CDCl_3$) δ9.16 (1H, s, C9-H), 9.07 (1H, d, J6.0 Hz, C7-H), 7.81 (1H, d, J6.0 Hz, C6-H), 4.82 (2H, m. $pyCH_2$), 3.44 (1H, d, J8.4 Hz, C9b-H), 2.29 (3H, s, $NCH_3$), 1.50–3.10 (9H, m, $CH_2$+CH), 1.95 (2H, m, $pyCH_2CH_2$), 1.00–1.40 (16H, m, 8×$CH_2$), 0.76 (3H, t, J6.9 Hz, $CH_2CH_3$); $^{13}$C NMR (75 MHz, $CDCl_3$) δ161.5, 143.2, 142.4, 138.8, 127.5, 63.1, 61.0, 55.7, 41.0, 35.6, 32.0, 31.8, 30.0, 29.51, 29.48, 29.4, 29.2, 29.1, 28.1, 27.3, 26.0, 22.6, 14.1.

EXAMPLE 5

Preparation of cis-8-Dodecyl-1-methyl-2,3,3a,4,5,9b-hexahydro-1H-pyrrolo[3,2-h]-isoquinolin-8-ium iodide (ACDD)

To a stirred solution of cis-1-methyl-2,3,3a,4,5,9b-hexahydro-1H-pyrrolo[3,2-h]isoquinoline (120 mg, 0.64 mmol) in AcOH (2 ml) was added 1-iodoundecane (569 mg, 1.92 mmol). The mixture was heated at reflux under nitrogen for 3 days. AcOH was evaporated and the residue was dissolved in $CHCl_3$. The mixture was washed with saturated aqueous $NaHCO_3$, water and brine successively and dried. Evaporation of the solvent followed by titration with ether afforded 205 mg (66%) of cis-8-dodecyl-1-methyl-2,3,3a,4,5,9b-hexahydro-1H-pyrrolo[3,2-h]isoquinolin-8-ium iodide (ACDD) as a brown oil. $^1$H NMR (300 MHz, $CDCl_3$) δ9.08 (1H, s, C9-H), 9.02 (1H, d, J6.3 Hz, C7-H), 7.79 (1H, d, J6.3 Hz, C6-H), 4.90 (2H, m. $pyCH_2$), 3.48 (1H, d, J8.4 Hz, C9b-H), 2.36 (3H, s, $NCH_3$), 1.50–3.10 (9H, m, $CH_2$+CH), 2.00 (2H, m, $pyCH_2CH_2$), 1.10–1.40 (18H, m, 9×$CH_2$), 0.85 (3H, t, J6.9 Hz, $CH_2CH_3$); $^{13}$C NMR (75 MHz, $CDCl_3$) δ161.5, 143.3, 142.5, 138.8, 127.5, 63.1, 61.0, 55.7, 41.0, 35.6, 32.0, 31.9, 30.0, 29.6×2, 29.5, 29.4, 29.3, 29.1, 28.1, 27.3, 26.0, 22.7, 14.1.

EXAMPLE 6

Preparation of cis-1-Methyl-6-octyl-2,3,3a,4,5,9b-hexahydro-1H-pyrrolo[2,3-f]-isoquinolin-6-ium iodide (BCO)

To a stirred solution of cis-1-methyl-2,3,3a,4,5,9b-hexahydro-1H-pyrrolo[2,3-f]isoquinoline (120 mg, 0.64 mmol) in AcOH (2 ml) was added 1-iodooctane (460 mg, 1.92 mmol). The mixture was heated at reflux under nitrogen for 3 days. AcOH was evaporated and the residue was dissolved in $CHCl_3$. The mixture was washed with saturated aqueous $NaHCO_3$, water and brine successively and dried. Evaporation of the solvent followed by titration with ether afforded 155 mg (57%) of cis-1-methyl-6-octyl-2,3,3a,4,5,9b-hexahydro-1H-pyrrolo[2,3-f]isoquinolin-6-ium iodide (BCO) as a brown oil. $^1$H NMR (300 MHz, $CDCl_3$) δ9.38 (1H, d, J6.0 Hz, C7-H), 8.20 (1H, d, J7.5 Hz, C9-H), 7.95 (1H, t, J7.0 Hz, C8-H), 4.82 (2H, m. py$CH_2$), 3.36 (1H, d, J8.4 Hz, C9b-H), 2.25 (3H, s, $NCH_3$), 1.62–3.20 (11H, m, $CH_2$+CH), 100–1.50 (10H, m, 5×$CH_2$), 0.82 (3H, t, J6.9 Hz, $CH_2CH_3$); $^{13}$C NMR (75 MHz, $CDCl_3$) δ157.0, 145.8, 144.8, 139.0, 125.3, 66.3, 59.0, 55.6, 40.6, 35.4, 31.8, 31.0, 29.7, 29.2, 29.1, 28.3, 26.4, 24.6, 22.7, 14.2.

EXAMPLE 7

Preparation of cis-1-Methyl-6-nonyl-2,3,3a,4,5,9b-hexahydro-1H-pyrrolo[2,3-f]-isoquinolin-6-ium iodide (BCN)

To a stirred solution of cis-1-methyl-2,3,3a,4,5,9b-hexahydro-1H-pyrrolo[2,3-f]isoquinoline (100 mg, 0.53 mmol) in AcOH (2 ml) was added 1-iodononane (407 mg, 1.59 mmol). The mixture was heated at reflux under nitrogen for 3 days. AcOH was evaporated and the residue was dissolved in $CHCl_3$. The mixture was washed with saturated aqueous $NaHCO_3$, water and brine successively and dried. Evaporation of the solvent followed by titration with ether afforded 110 mg (47%) of cis-1-methyl-6-nonyl-2,3,3a,4,5,9b-hexahydro-1H-pyrrolo[2,3-f]isoquinolin-6-ium iodide (BCN) as a brown oil. $^1$H NMR (300 MHz, $CDCl_3$) δ9.38 (1H, d, J6.0 Hz, C7-H), 8.17 (1H, d, J7.5 Hz, C9-H), 7.93 (1H, t, J7.0 Hz, C8-H), 4.82 (2H, m. py$CH_2$), 3.31 (1H, d, J8.4 Hz, C9b-H), 2.24 (3H, s, $NCH_3$), 1.62–3.20 (11H, m, $CH_2$+CH), 1.10–1.50 (12H, m, 6×$CH_2$), 0.80 (3H, t, J6.6 Hz, $CH_2CH_3$); $^{13}$C NMR (75 MHz, $CDCl_3$) δ156.9, 145.7, 144.6, 139.0, 125.2, 66.2, 58.9, 55.6, 40.6, 35.3, 31.8, 30.9, 29.7, 29.3, 29.2×2, 28.3, 26.3, 24.5, 22.7, 14.1.

EXAMPLE 8

Preparation of cis-6-Decyl-1-methyl-2,3,3a,4,5,9b-hexahydro-1H-pyrrolo[2,3-f]-isoquinolin-6-ium iodide (BCD)

To a stirred solution of cis-1-methyl-2,3,3a,4,5,9b-hexahydro-1H-pyrrolo[2,3-f]isoquinoline (100 mg, 0.53 mmol) in AcOH (2 ml) was added 1-iododecane (428 mg, 1.59 mmol). The mixture was heated at reflux under nitrogen for 3 days. AcOH was evaporated and the residue was dissolved in $CHCl_3$. The mixture was washed with saturated aqueous $NaHCO_3$, water and brine successively and dried. Evaporation of the solvent followed by titration with ether afforded 106 mg (44%) of cis-6-decyl-1-methyl-2,3,3a,4,5,9b-hexahydro-1H-pyrrolo[2,3f]isoquinolin-6-ium iodide (BCD) as a brown oil. $^1$H NMR (300 MHz, $CDCl_3$) δ9.34 (1H, d, J6.3 Hz, C7-H), 8.20 (1H, d, J7.5 Hz, C9-H), 7.93 (1H, t, J6.9 Hz, C8-H), 4.80 (2H, m. py$CH_2$), 3.38 (1H, d, J8.1 Hz, C9b-H), 2.23 (3H, s, $NCH_3$), 1.64–3.30 (11H, m, $CH_2$+CH), 1.10–1.50 (14H, m, 7×$CH_2$), 0.80 (3H, t, J6.6 Hz, $CH_2CH_3$); $^{13}$C NMR (75 MHz, $CDCl_3$) δ156.9, 145.8, 144.6, 138.8, 125.3, 66.2, 58.9, 55.5, 40.5, 35.3, 31.9, 30.9, 29.6, 29.5, 29.4, 29.3, 29.2, 28.2, 26.3, 24.6, 22.7, 14.1.

EXAMPLE 9

Preparation of cis-1-Methyl-6-undecyl-2,3,3a,4,5,9b-hexahydro-1H-pyrrolo[2,3-f]-isoquinolin-6-ium iodide (BCU)

To a stirred solution of cis-1-methyl-2,3,3a,4,5,9b-hexahydro-1H-pyrrolo[2,3-f]isoquinoline (80 mg, 0.43 mmol) in AcOH (2 ml) was added 1-iodoundecane (361 mg, 1.29 mmol). The mixture was heated at reflux under nitrogen for 3 days. AcOH was evaporated and the residue was dissolved in $CHCl_3$. The mixture was washed with saturated aqueous $NaHCO_3$, water and brine successively and dried. Evaporation of the solvent followed by titration with ether afforded 90 mg (45%) of cis-1-methyl-6-undecyl-2,3,3a,4,5,9b-hexahydro-1H-pyrrolo[2,3-f]isoquinolin-6-ium iodide (BCU) as a brown oil. $^1$H NMR (300 MHz, $CDCl_3$) δ9.39 (1H, d, J6.3 Hz, C7-H), 8.19 (1H, d, J7.8 Hz, C9-H), 7.94 (1H, t, J6.9 Hz, C8-H), 4.82 (2H, m. py$CH_2$), 3.34 (1H, d, J8.4 Hz, C9b-H), 2.23 (3H, s, $NCH_3$), 1.65–3.30 (11H, m, $CH_2$+CH), 1.10–1.50 (16H, m, 8×$CH_2$), 0.82 (3H, t, J6.6 Hz, $CH_2CH_3$); $^{13}$C NMR (75 MHz, $CDCl_3$) δ156.9, 145.9, 144.7, 139.0, 125.3, 66.3, 59.0, 55.6, 40.6, 35.4, 32.0, 31.0, 29.69, 29.65, 29.61, 29.5, 29.4, 29.2, 28.3, 26.4, 24.6, 22.8, 14.2.

EXAMPLE 10

Preparation of cis-6-Dodecyl-1-methyl-2,3,3a,4,5,9b-hexahydro-1H-pyrrolo[2,3-f]-isoquinolin-6-ium iodide (BCDD)

To a stirred solution of cis-1-methyl-2,3,3a,4,5,9b-hexahydro-1H-pyrrolo[2,3-f]isoquinoline (100 mg, 0.53 mmol) in AcOH (2 ml) was added 1-iodoundecane (474 mg, 1.59 mmol). The mixture was heated at reflux under nitrogen for 3 days. AcOH was evaporated and the residue was dissolved in $CHCl_3$. The mixture was washed with saturated aqueous $NaHCO_3$, water and brine successively and dried. Evaporation of the solvent followed by titration with ether afforded 116 mg (45%) of cis-6-dodecyl-1-methyl-2,3,3a,4,5,9b-hexahydro-1H-pyrrolo[2,3-f]isoquinolin-6-ium iodide (BCDD) as a brown oil. $^1$H NMR (300 MHz, $CDCl_3$) δ9.40 (1H, d, J6.0 Hz, C7-H), 8.17 (1H, d, J7.8 Hz, C9-H), 7.94 (1H, t, J6.9 Hz, C8-H), 4.84 (2H, m. py$CH_2$), 3.31 (1H, d, J8.4 Hz, C9b-H), 2.22 (3H, s, $NCH_3$), 1.64–3.30 (11 H, m, $CH_2$+CH), 1.10–1.50 (18H, m, 5×$CH_2$), 0.82 (3H, t, J6.6 Hz, $CH_2CH_3$); $^{13}$C NMR (75 MHz, $CDCl_3$) δ156.6, 145.7, 144.8, 139.0, 125.3, 66.3, 59.0, 55.6, 40.6, 35.4, 32.0, 31.0, 29.7×3, 29.6, 29.5, 29.4, 29.3, 28.4, 26.4, 24.6, 22.8, 14.2.

EXAMPLE 11

[$^3$H]-DA Release Assay

Rat striatal slices (500 μm thickness, 6–8 mg wet weight) were incubated for 30 minutes in Kreb's buffer (118 nM NaCl, 4.7 nM KCl, 1.2 nM $MgCl_2$, 1.0 nM $NaH_2PO_4$, 1.3 nM $CaCl_2$, 11.1 nM glucose, 25 nM $NaHCO_3$, 0.1.1 nM L-ascorbic acid, and 0.004 nM disodium EDTA; pH 7.4, and saturated with 95% $O_2$/5% $CO_2$) in a metabolic shaker at 34° C. Slices were rinsed with 15 ml of fresh buffer and incubated for an additional 30 minutes in fresh buffer containing 0.1 μM [³H]-DA (6 slices/3 ml). Subsequently, slices were rinsed with 15 ml of fresh buffer and transferred to a glass superfusion chamber. Slices were superfused (1.0 ml/min) for 60 minutes with Kreb's buffer containing nomifensine (10 μM and pargyline (10 μM) and maintained at 34° C., pH 7.4, with continual aeration (95% $O_2$/5% $CO_2$). Two 5 minute samples (5 ml each) were collected to determine basal outflow of [³H]-DA. N-Substituted conformationally restricted nicotine analogs were added to the superfusion buffer after the collection of the second sample and remained in the buffer until 12 consecutive 5 minute samples were collected. Subsequently, S-(−)-nicotine (10 μM) was added to the buffer and an additional 12 consecutive five minute samples were collected. At the end of the experiment, each slice was solubilized and the [³H] content of the tissue determined.

Radioactivity in the superfusate and tissue samples was determined by liquid scintillation spectroscopy. Fractional release for each tritium collected in each sample by the total tritium present in the tissue at the time of sample collection and was expressed as a percentage of total tritium. Basal [³H]outflow was calculated from the average of the tritium collected in the two five minute samples just before addition of the conformationally restricted nicotine analog. The sum of the increase in collected tritium resulting from either exposure to the test compound or exposure to nicotine in the absence and presence of the test compound equaled total [³H]overflow. [³H]Overflow was calculated by subtracting the [³H]outflow during an equivalent period of prestimulation from the values in samples collected during and after drug exposure. Inasmuch as the radiolabelled compounds were not separated and identified, the tritium collected in superfusate is referred to as either [³H]outflow or [³H] overflow, rather than as [³H]-DA. [³H]Overflow primarily represents [³H]-DA in the presence of nomifensine and pargyline in the superfusion buffer.

The conformationally restricted nicotine analogs were evaluated for their ability to evoke [³H] release from rat striatal slices at two concentrations (0.1 and 1 μM). In addition, the classical competitive nicotinic antagonist DHBE was also examined in this assay for comparison. None of the compounds examined had any significant [³H]-DA releasing properties in this assay at concentrations below 10 μM, but all the compounds exhibited intrinsic activity at 10 μM Since striatal NIC-evoked [³H]-DA: release is thought to be mediated through a mechanism involving the α3β2-containing receptor subtype, these compounds do not possess significant agonist activity below 10 μM at this putative receptor subtype.

The conformationally restricted bridged NONI analogs were also evaluated for their ability to inhibit NIC evoked [³H]-DA release. In these experiments, the striatal slices were superfused for 60 minutes with various concentrations of the analogs prior to NIC (10 μM) exposure. Antagonist activity was evaluated by comparing the NIC-evoked [³H] overflow in the absence and presence of the analogs. The potency of these bridged NONI analogs for inhibition of NIC-evoked [³H]-DA release from rat striatal slices is illustrated in Table 1 by a comparison of their $IC_{50}$ values.

TABLE 1

Comparative $IC_{50}$s for Syn and Anti Rotamer Analogs in the S-(−)-NIC-evoked [³H]DA Release Assay[a]

| Compd | $IC_{50}$ (nM) |
|---|---|
| ACO (R = n-$C_8H_{17}$) | 688 |
| ACN (R = n-$C_9H_{19}$) | 265 |
| ACD (R = n-$C_{10}H_{21}$) | 200 |
| ACU (R = n-$C_{11}H_{23}$) | 51 |
| ACDD (R = n-$C_{12}H_{25}$) | 88 |
| BCO (R = n-$C_8H_{17}$) | 127 |
| BCN (R = n-$C_9H_{19}$) | 201 |
| BCD (R = n-$C_{10}H_{21}$) | 54 |
| BCU (R = n-$C_{11}H_{23}$) | 299 |
| BCDD (R = n-$C_{12}H_{25}$) | 1580 |

[a]No significant intrinsic agonist activity was observed for any of these compounds in this assay below 10 μM.

EXAMPLE 12

[³H]-NIC Binding Assay

Striata from two rats were dissected, pooled, and homogenized with a Tekmar polytron in 10 vol of ice-cold modified Krebs-HEPES buffer (20 mM HEPES, 118 mM NaCl, 4.8 mM KCl, 2.5 mM $CaCl_2$, 1.2 mM $MgSO_4$, adjusted to pH 7.5). The homogenates were incubated at 37° C. for 5 minutes and centrifuged at 15,000 g for 20 minutes. The pellet was resuspended in 10 volumes of ice-cold MilliQ water, incubated for 5 minutes at 37° C., and centrifuged at 15,000 g for 20 minutes. The second pellet was then resuspended in 10 volumes of fresh ice-cold 10% Krebs-HEPES buffer, incubated at 37° C., and centrifuged at 15,000 g for 20 minutes. The latter sequence of resuspension, incubation, and centrifugation was repeated. The pellet was frozen under fresh 10% Krebs-HEPES buffer and stored at −40° C. until assayed. Upon assay, the pellet was resuspended in the Krebs-HEPES buffer, incubated at 37° C. for 5 minutes, and centrifuged at 15,000 g for 20 minutes. The final pellet was resuspended in 3.6 ml ice-cold MilliQ water which provided for approximately 200 μg protein per 100 μl aliquot. Competition assays were performed in triplicate in a final volume of 200 μl Krebs-HEPES buffer containing 250 mmol Tris buffer (pH 7.5 at 4° C.). Reactions were initiated by addition of 100 μl of membrane suspension to 3 mM [³H]-NIC (50 μl). and one of at least nine concentrations of analog (50 μl). After a 90 minutes incubation at 40° C., reactions were terminated by dilution of the samples with 3 ml of ice-cold Krebs-HEPES buffer followed immediately by filtration through Whatman GF/B. glass fiber filters (presoaked in 0.5% polyethyleneimine) using a Brandel Cell Harvester. Filters were rinsed three times with. 3 ml of ice-cold Krebs-HEPES buffer, transferred to scintillation vials, and 5 ml scintillation cocktail (Research Products International Corp., Mt. Prospect, Ill.) added. Nonspecific binding determined in triplicate was defined as binding in the presence of 10 $\mu$M NIC. Binding parameters were determined using the weighted, least squares regression.

The conformationally restricted nicotine analogs were evaluated for their ability to displace [$^3$H]-NIC binding from rat striatal membranes. The results are summarized in Table 2. Furthermore, the displacement by the analogs was compared to those produced by NONI, NDNI, and DH$\beta$E. All of the compounds examined displaced [$^3$H]-NIC binding with much lower affinities than DH$\beta$E. The 8-carbon alkyl chain bridged nicotinium compounds (ACO and BCO) had much lower affinity for the [$^3$H]-NIC binding site compared to NONI; surprisingly, the 10-carbon alkyl chain bridged nicotiniumr compounds (ACD and BCD) lost their ability to interact with this binding site compared to the high affinity of NDNI. Thus, the unique conformationally restricted stereochemistry presented by these analogs to the $\alpha4\beta2$-containing receptor subtype is not recognized by this subtype.

TABLE 2

Specific Binding of [$^3$H]-NIC to Rat Striatal Nicotinic Acetylcholine Receptors in the Presence of Conformationally Constrained NONI Analogs

| | Concentration ($\mu$M)[a] | | | |
|---|---|---|---|---|
| Compound | 0 | 1 | 10 | 100 |
| NONI | 42.0 ± 3.0 | 42.6 ± 2.6 | 37.5 ± 2.3 | 14.0 ± 1.3 |
| NDNI | 42.0 ± 3.3 | 9.2 ± 1.0 | 0.5 ± 0.2 | ND[b] |
| DHBE | 55.0 ± 3.0 | 18.0 ± 5.0 | 4.0 ± 1.0 | ND |
| ACO | 43.4 ± 1.0 | 44.5 ± 0.4 | 42.2 ± 0.5 | 30.2 ± 6.9 |
| ACN | 51.2 ± 2.9 | 49.8 ± 3.6 | 48.9 ± 2.9 | 30.2 ± 2.2 |
| ACD | 50.9 ± 2.7 | 50.3 ± 3.7 | 52.1 ± 2.6 | 37.0 ± 1.7 |
| ACU | 47.1 ± 2.1 | 51.3 ± 2.0 | 49.0 ± 0.3 | 42.7 ± 2.1 |
| ACDD | 44.7 ± 1.7 | 49.5 ± 0.7 | 49.8 ± 2.9 | 44.5 ± 1.7 |
| BCO | 51.2 ± 1.5 | 50.5 ± 1.2 | 39.7 ± 1.4 | 13.5 ± 0.5 |
| BCN | 48.0 ± 2.9 | 49.6 ± 1.2 | 47.7 ± 2.1 | 36.2 ± 0.3 |
| BCD | 53.7 ± 0.5 | 54.9 ± 0.7 | 54.4 ± 1.1 | 47.9 ± 2.8 |
| BCU | 53.7 ± 0.5 | 56.1 ± 0.6 | 53.9 ± 1.2 | 37.3 ± 1.8 |
| BCDD | 45.8 ± 3.9 | 43.7 ± 4.5 | 43.0 ± 4.7 | 34.0 ± 2.1 |

[a]Data are expressed as fmol/mg of protein, mean ± S.E.M of 3 independent experiments. Specific binding is calculated as the difference between the total binding of 3 nM [$^3$H]-NIC to the receptors alone and its nonspecific binding in the presence of 10 $\mu$M cold nicotine.
[b]ND: Not determined.

EXAMPLE 13

[$^3$H]-MLA Binding Assay

Naïve male Sprague-Dawley rats weighing 220–250 g were housed two per cage with free access to food and water. All procedures in these studies were approved by the Institutional Animal Care and Use Committee at the University of Kentucky. The animals were killed by decapitation, each brain was quickly removed and placed on ice-cold glass platform. The brain was dissected into the whole brain tissue without cortex, striatum and cerebellum and was frozen in liquid nitrogen and stored at −70° C. until use.

The brain tissue was homogenized with a Tekmar Polytron (setting 40) in 20 volumes of ice-cold hypotonic buffer (2 mM HEPES, 14.4 mM NaCl, 0.15 mM KCl, 0.2 mM CaCl$_2$ and 0.1 mM MgSO$_4$, pH=7.5). The homogenate was incubated at 37° C. for 10 minutes and centrifuged at 25,000×g for 15 minutes at 40° C. The pellet was washed 3 times more by resuspension in the 20 volumes of the same buffer and centrifugation at the above parameters. The final pellet was stored at −20° C. under 4.6 ml of the incubation buffer and was suspended just before the incubation with radioligand.

The binding of [$^3$H]methyllycaconitine ([$^3$H]MLA) to probe $\alpha$7-type neuronal nicotinic acetylcholine receptors was measured using a modification of the method of Davies et al., "Characterisation of the binding of [$^3$H] methyllycaconitine: a new radioligand for labelling $\alpha$7-type neuronal nicotinic acetylcholine receptors,' Neuropharmacology, 38, 679–690 (1999). [$^3$H]-MLA (25.4 Ci/mmol) was purchased from Tocris Cookson Ltd., Bristol, U.K. Binding was performed in duplicate, in a final volume of 250 $\mu$l of the incubation medium, containing 20 mM HEPES, 144 mM NaCl, 1.5 mM KCl, 2 mM CaCl$_2$, 1 mM MgSO$_4$ and 0.05% BSA, pH=7.5. Reaction was initiated by the addition of 100 $\mu$l of membrane suspension to the samples containing a desired concentration t of test compounds and 2.5 mM [$^3$H]-MLA (final concentration) and incubated for 2 hours at room temperature. Total binding was measured in the absence of unlabelled ligand and nonspecific binding was determined in the presence of 1 $\mu$M unlabelled MLA. The binding reaction was terminated by dilution of samples with 3 ml of ice-cold incubation buffer followed by immediate filtration through presoaked in 0.5% polyetylenimine glass fiber filters (S&S, grade #32) using a Brandel harvester system. Filters were rinsed three times with 3 ml of ice-cold buffer, transferred to scintillation vials and 4 ml of scintillation cocktail was added. Protein was measured using the Bradford dye-binding procedure with bovine serum albumin as the standard.

In order to determine if these compounds have selectivity at the $\alpha$3$\beta$2 receptor subtype, the bridged NONI analogs were evaluated for their ability to displace [$^3$H]-MLA binding from rat brain membranes, as a reflection of their interaction with the $\alpha$7 receptor (Table 3). In addition, the classical $\alpha$7 receptor antagonist $\alpha$-bungarotoxin was also examined in this assay for comparison. $\alpha$-Bungarotoxin afforded a Ki value of 28.6±5.4 nM in the above assay. The results from the competition binding assay showed that none of the conformationally constrained compounds possessed any significant binding affinity in the [$^3$H]-MLA assay. The percentage control of 2.5 nM [$^3$H]-MLA binding to the rat brain membrane preparation in the presence of 10 $\mu$M of bridged NONI analogs ranged from 92.3 to 101.9, indicating that at a 10 $\mu$M concentration, the above compounds had no significant affinity for the $\alpha$7 receptor subtype.

TABLE 3

[$^3$H]-MLA Binding in the Presence of Conformationally Restrained NONI and NDNI Analogs

| Compound | % Control [$^3$H]-MLA Binding at 10 $\mu$M* |
|---|---|
| ACO | 91.5 |
| ACN | 100.7 |
| ACD | 101.9 |
| ACU | 100.4 |
| ACDD | 101.9 |
| BCO | 93.6 |
| BCN | 94.0 |
| BCD | 96.2 |

TABLE 3-continued

[³H]-MLA Binding in the Presence of Conformationally Restrained NONI and NDNI Analogs

| Compound | % Control [³H]-MLA Binding at 10 µM* |
|---|---|
| BCU | 92.3 |
| BCDD | 94.2 |

*Data are expressed as % whole brain binding relative to control (2.5 nM [³H]-MLA).

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. A compound of the following III or IV;

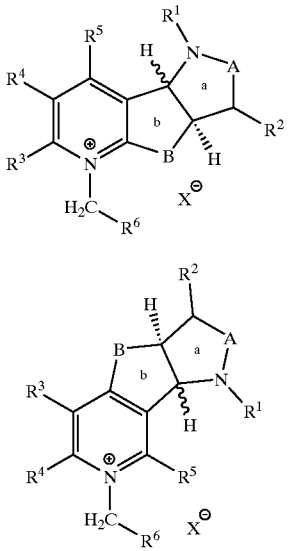

wherein

A and B each independently represent $CH_2$ or $CH_2CH_2$;

$R^1$ represents hydrogen, lower alkyl or an aromatic group-containing species;

$R^2$ represents hydrogen or lower alkyl;

$R^3$, $R^4$ and $R^5$ each independently represent hydrogen; alkyl; substituted alkyl; cycloalkyl; substituted cycloalkyl; alkenyl; substituted alkenyl; alkynyl; substituted alkynyl; aryl, substituted aryl; alkylaryl; substituted alkylaryl; arylalkyl; substituted arylalkyl; arylalkenyl; substituted arylalkenyl; arylalkynyl; substituted arylalkynyl; heterocyclic; substituted heterocyclic; trifluoromethyl; halogen; cyano; nitro; $S(O)Y^2$, $S(O)_2Y^2$, $S(O)_2OY^2$ or $S(O)_2NHY^2$, wherein each $Y^2$ is hydrogen, lower alkyl, alkenyl, alkynyl or aryl, provided that when $R^3$, $R^4$ or $R^5$ is $S(O)Y^2$, $Y^2$ is not hydrogen, and further provided that when $Y^2$ is alkenyl or alkynyl, the site of unsaturation is not conjugated with a heteroatom; $C(O)Y^3$, wherein $Y^3$ is hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, arylalkenyl, substituted arylalkenyl, arylalkynyl, substituted arylalkynyl, heterocyclic, substituted heterocyclic or trifluoromethyl, provided, however, that the carbonyl functionality is not conjugated with an alkenyl or alkynyl functionality; $OY^4$ or $N(Y^4)_2$ wherein $Y^4$ is hydrogen, alkyl, substituted alkyl, cycloalkyl, substituted cycloalkyl, alkenyl, subtituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, acyl, trifluoromethyl, alkylsulfonyl or arylsulfonyl, provided that the $OY^4$ or $N(Y^4)_2$ functionality is not conjugated with an alkenyl or alkynyl functionality; $SY^5$ wherein $Y^5$ is hydrogen, alkyl, substituted alkyl, cycloalkyl, substituted cycloalkyl, alkenyl, subtituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic or trifluoromethyl, provided that the $SY^5$ functionality is not conjugated with an alkenyl or alkynyl functionality;

$R^6$ represents alkyl, substituted alkyl, cycloalkyl, substituted cycloalkyl, alkenyl, subtituted alkenyl, alkynyl, substituted alkynyl, aryl, substituted aryl, arylalkyl, substituted arylalkyl, arylalkenyl, substituted arylalkenyl, arylalkynyl, substituted arylalkynyl, heterocyclic or substituted heterocyclic; and X represents chlorine, bromine, iodine, $HSO_4$, $1/2SO_2$, $CH_3SO_3$, p-TsO or $CF_3SO_3$.

2. The compound according to claim 1, wherein $R^1$ is $C_1$–$C_{10}$alkyl.

3. The compound according to claim 1, wherein $R^1$ is $C_1$–$C_6$alkyl.

4. The compound according to claim 1, wherein $R^1$ is methyl.

5. The compound according to claim 1, wherein $R^1$ is ethyl.

6. The compound according to claim 1, wherein $R^1$ is isopropyl.

7. The compound according to claim 1, wherein $R^1$ is isobutyl.

8. The compound according to claim 1, wherein $R^2$ is hydrogen.

9. The compound according to claim 1, wherein $R^3$, $R^4$ and $R^5$ are individually selected from hydrogen, halogen, alkyl, or alkanoyl.

10. The compound according to claim 1, wherein $R^6$ is a $C_4$–$C_{19}$ unbranched alkyl.

11. The compound according to claim 1, wherein X is iodine.

12. The compound according to claim 1, wherein said compound is cis-1-methyl-8-octyl-2,3,3a,4,5,9b-hexahydro-1H-pyrrolo[3,2-h]isoquinolin-8-ium iodide (ACO).

13. The compound according to claim 1, wherein said compound is cis-1-methyl-8-nonyl-2,3,3a,4,5,9b-hexahydro-1H-pyrrolo[3,2-h]isoquinolin-8-ium iodide (ACN).

14. The compound according to claim 1, wherein said compound is cis-8-decyl-1-methyl-2,3,3a,4,5,9b-hexahydro-1H-pyrrolo[3,2-h]isoquinolin-8-ium iodide (ACD).

15. The compound according to claim 1, wherein said compound is cis-1-methyl-8-undecyl-2,3,3a,4,5,9b-hexahydro-1H-pyrrolo[3,2-h]isoquinolin-8-ium iodide (ACU).

16. The compound according to claim 1, wherein said compound is cis-8-dodecyl-1-methyl-2,3,3a,4,5,9b-hexahydro-1H-pyrrolo[3,2-h]isoquinolin-8-ium iodide (ACDD).

17. The compound according to claim 1, wherein said compound is cis-1-methyl-6-octyl-2,3,3a,4,5,9b-hexahydro-1H-pyrrolo[2,3-f]isoquinolin-8-ium iodide (BCO).

18. The compound according to claim 1, wherein said compound is cis-1-methyl-6-nonyl-2,3,3a,4,5,9b-hexahydro-1H-pyrrolo[2,3-f]isoquinolin-6-ium iodide (BCN).

19. The compound according to claim 1, wherein said compound is cis-6-decyl-1-methyl-2,3,3a,4,5,9b-hexahydro-1H-pyrrolo[2,3-f]isoquinolin-6-ium iodide (BCD).

20. The compound according to claim 1, wherein said compound is cis-1-methyl-6-undecyl-2,3,3a,4,5,9b-hexahydro-1H-pyrrolo[2,3-f]isoquinolin-6-ium iodide (BCU).

21. The compound according to claim 1, wherein said compound is cis-6-dodecyl-1-methyl-2,3,3a,4,5,9b-hexahydro-1H-pyrrolo[2,3-f]isoquinolin-6-ium iodide (BCDD).

22. A compound according to claim 1, wherein the ring junction between a and b rings is cis or trans.

23. A compound according to claim 1, wherein said compound is substantially optically pure.

24. A compound according to claim 1, wherein said compound is a racemic mixture or a diastereometric mixture.

25. A method of binding a nicotine receptor with a compound according to claim 1, wherein said compound is a nicotinic receptor antagonist.

26. A method of binding a nicotine receptor with a compound according to claim 1, wherein said compound inhibits NIC-evoked [$^3$H]-DA release.

27. A method of binding a nicotine receptor with a compound according to claim 1, wherein said compound inhibits [$^3$]-NIC binding.

28. A method of inhibiting the binding of a nicotinic receptor comprising the step of administering of a pharmaceutically effective amount of a compound according to claim 1.

29. A method of treating abuse of nicotinic receptor agonists, addiction to tobacco products, or addiction to nicotine comprising the step of administering an effective amount of a compound according to claim 1.

30. A method of treating Alzheimer's disease comprising the step of administering of a pharmaceutically effective amount of a compound according to claim 1.

31. A method of treating Parkinson's disease comprising the step of administering of a pharmaceutically effective amount of a compound according to claim 1.

32. A method of treating pain, comprising the step of administering of a pharmaceutically effective amount of a compound according to claim 1.

33. A method of binding a nicotine receptor with a compound according to claim 1, wherein said compound competitively inhibits central nervous system acting nicotinic receptor agonists.

34. A method of binding a nicotine receptor with a compound according to claim 1, wherein said compound acts at the putative $\alpha 3\beta 2$ neuronal nicotinic receptor in the central nervous system.

35. A method of treating irritable bowel syndrome, comprising the step of administering of a pharmaceutically effective amount of a compound according to claim 1.

36. A method of treating calitis, comprising the step of administering of a pharmaceutically effective amount of a compound according to claim 1.

* * * * *